United States Patent [19]

Bartlett

[11] 4,423,622

[45] Jan. 3, 1984

[54] PIPE PRESSURE TESTING AND CLEANING APPARATUS

[75] Inventor: John M. Bartlett, Weston-on-the-Green, England

[73] Assignee: Elan Pressure Clean Limited, Coventry, England

[21] Appl. No.: 325,425

[22] PCT Filed: Mar. 23, 1981

[86] PCT No.: PCT/GB81/00053

§ 371 Date: Nov. 20, 1981

§ 102(e) Date: Nov. 20, 1981

[87] PCT Pub. No.: WO81/02787

PCT Pub. Date: Oct. 1, 1981

[30] Foreign Application Priority Data

Mar. 22, 1980 [GB] United Kingdom ............ 8009768

[51] Int. Cl.³ ........................................... G01M 3/28
[52] U.S. Cl. .................................... 73/49.5; 15/304
[58] Field of Search ............. 73/49.1, 49.5; 15/302, 15/304; 138/97

[56] References Cited

U.S. PATENT DOCUMENTS

| 2,633,739 | 4/1953 | Potts et al. ............ 73/49.5 |
| 2,689,475 | 9/1954 | Blanton . |
| 3,536,263 | 10/1970 | Parker . |
| 3,537,299 | 11/1970 | Girard . |
| 3,566,675 | 3/1971 | Ledebur ............ 73/49.5 |
| 3,760,632 | 9/1973 | Illyes . |
| 3,765,050 | 11/1973 | Van Allman et al. . |
| 3,877,293 | 4/1975 | McKeage ............ 73/49.5 X |
| 4,157,096 | 6/1979 | Miller . |
| 4,182,160 | 1/1980 | Powers et al. . |
| 4,192,177 | 3/1980 | Crickard et al. ............ 73/49.5 |

FOREIGN PATENT DOCUMENTS

| 692833 | 8/1964 | Canada ............ 73/49.5 |
| 2441358 | 3/1976 | Fed. Rep. of Germany . |
| 2335786 | 7/1977 | France . |
| 1510933 | 5/1978 | United Kingdom . |

*Primary Examiner*—S. Clement Swisher
*Assistant Examiner*—Joseph W. Roskos
*Attorney, Agent, or Firm*—John J. Byrne; Bradford E. Kile

[57] ABSTRACT

Method of an apparatus for pressure testing and cleaning pipe in which one or more pipes are secured to a treatment manifold (31). The or each pipe is then filled through one end with low pressure water via an inlet (40) in the manifold (31), the other end of the or each pipe including a self-bleeding valve (52) which closes once the air within the pipes has been evacuated. The pressure is held for a predetermined time and the pressure sensed by a visual gauge (14) and a paper read-out (16) so that any pressure drop indicative of failure is noted. The pressure is then released, the valve (52) removed and the high pressure water at a pressure between 500–8000 psi introduced through jets (35) to wash the pipes which are then dried with compressed air before removal.

14 Claims, 10 Drawing Figures

PIPE PRESSURE TESTING AND CLEANING APPARATUS

FIELD OF THE INVENTION

This invention relates to a method of treating pipes, particularly pressure testing and cleaning pipes and to apparatus for carrying out the method.

BRIEF DESCRIPTION OF THE PRIOR ART

At present pressure pipes are cleaned and pressure tested at separate stations. This means that the pipes have first to be cleaned by washing and drying and then are moved to pressure testing apparatus at a different location. The present arrangement therefore is unsatisfactory and time consuming. Moreover bleeding of the pipes during pressure testing is effected manually which is time consuming.

SUMMARY OF THE PRESENT INVENTION

According to the present invention there is provided a method of pressure testing and cleaning a pipe comprising the steps of, locating a first end of the pipe on a treatment manifold, supplying fluid to the pipe through the manifold, pressurising the pipe to a required desired value, sensing the pressure level within the pipe so as to register a pressure drop indicative of pipe failure, releasing the pressure within the pipe, and washing the pipe with water at high pressure above 500 psi supplied through the manifold.

Preferably the pipe is dried with air supplied to the pipe through manifold eg compressed air. The pressure fluid may be water supplied from the same source as the washing water but by a different line. The washing is preferably effected at high pressure between 500 psi and 8000 psi suitably about 4500 psi and low volume.

According to another aspect of the invention there is provided apparatus for pressure testing and cleaning a pipe comprising a treatment manifold, means for locating a first end of the pipe on the treatment manifold, means for supplying fluid to the pipe via said manifold, means for pressurising said fluid within the pipe, sensing means for sensing the pressure level within the pipe so as to register a pressure drop indicative of pipe failure, and means for washing the pipe with water at high pressure above 500 psi once the pressure test has been successfully completed.

Preferably the other end of the pipe is provided with a self-bleeding valve so as to bleed air automatically during pressure testing, the valve being closed on the pressure within the pipe exceeding a predetermined level.

The treatment manifold suitable comprises a main bore, a valve inlet to the main bore for high pressure water, a first plurality of apertures opening into the main bore each for receiving a pipe to be treated, a secondary bore, a second plurality of apertures opening into, the main bore and one into each of the first plurality of apertures, the means for supplying fluid to the pipe and the means for pressuring the fluid comprising first and second inlets into the secondary bore. The pressure within the pipe(s) during pressure testing is sensed by a visual gauge and a paper read-out so as to provide indication of pipe failure. The pressure sensing may be effected in any convenient known way eg electronically, the pressure varying a resistance within an electronic circuit proportional to the pressure changes.

The advantages of the present invention are that pressure testing, washing and drying can all be effected at the same station. Moreover, the provision of automatic bleed valves for bleeding air from the pipes during pressure testing means that manipulation by the operator is no longer required.

BRIEF DESCRIPTION OF THE DRAWINGS

The invention will now be described by way of example with reference to the accompanying drawings in which.

DESCRIPTION OF THE PREFERRED EMBODIMENT

In the drawings pipe treatment rig comprises a treatment chamber 1 having an upper, pipe-receiving area 2 and a lower, water collector tank 3 with a mesh cover 4. The treatment chamber 1 includes a releasable canopy 5 hinged at 6 to allow it to be opened for access to the pipe-receiving area 2 from the closed position to the position shown in dotted lines in FIG. 1. The canopy 5 is counter-balanced and includes a manually-operated fluorescent lighting strip 7 and a laminated glass viewing panel 8. The canopy is secured in position by toggle clamps (not shown) and is preferably electrically interlocked for safety.

Figure 1:
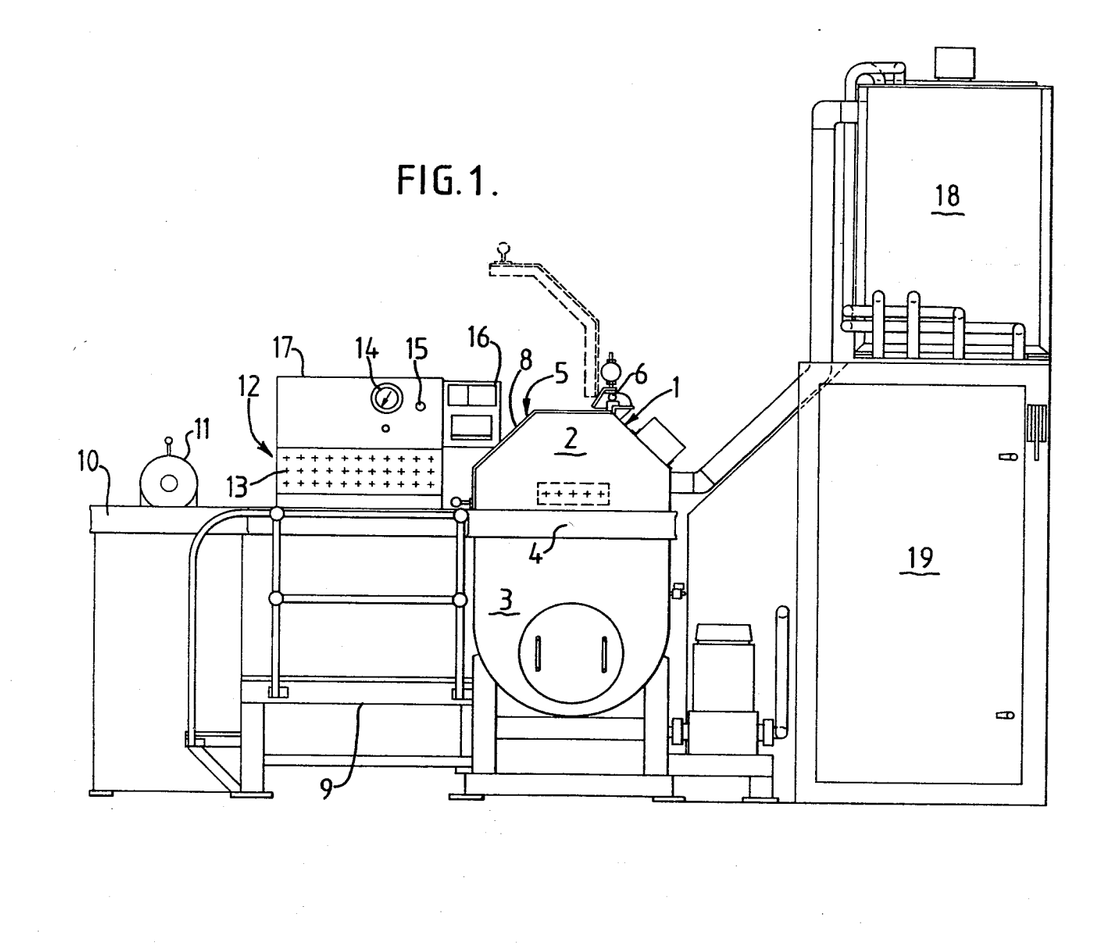
FIG. 1 is a side view of the preferred embodiment of pipe treatment apparatus in accordance with the invention.

FIG. 1 shows that the rig further includes an operator's working platform 9 which separates a sloping work table 10 from the treatment chamber 1. Positioned on the top, and at one end of the work table 10 is a pipe end cleaning attachment 11 shown in more detail in FIGS. 3 and 4. The sloping work table 10 is double skin, the top being perforated at its lower end and the bottom skin having a water outlet to the water collector tank 3. In use, water from the end cleaning attachment 11 passes between the skins to the water collector tank 3 as explained in more detail below. Any surplus water that should fall upon the top skin drains to the bottom skin through the perforations provided.

Located at one end of the operator's working platform 9 is a control panel 12 including general operating controls diagrammatically indicated 13 and in particular, a pressure check gauge 14, pressure test regulator 15, pressure test gauge and paper tape read out unit 16 and isolator button 17. Behind the treatment chamber 1 is a water header tank 18 supported upon the top of a sound-proof compartment 19. The sound-proof compartment includes the various pumps and filters described in more detail below.

Figure 3:
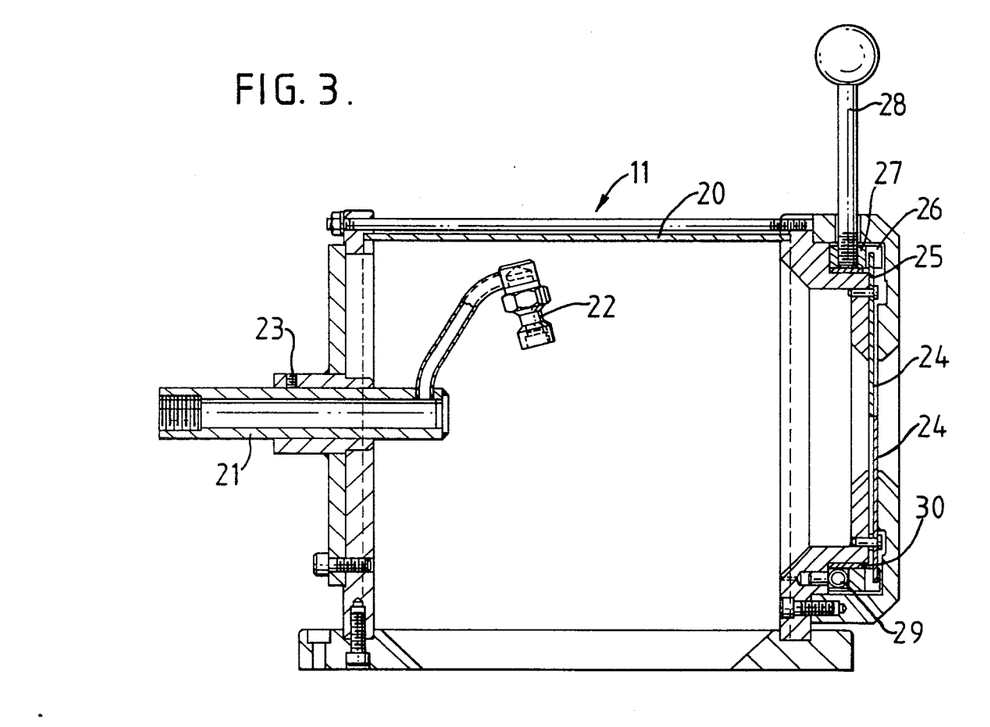
FIG. 3 is a sectional side elevation of the end cleaning attachment.
Figure 4:
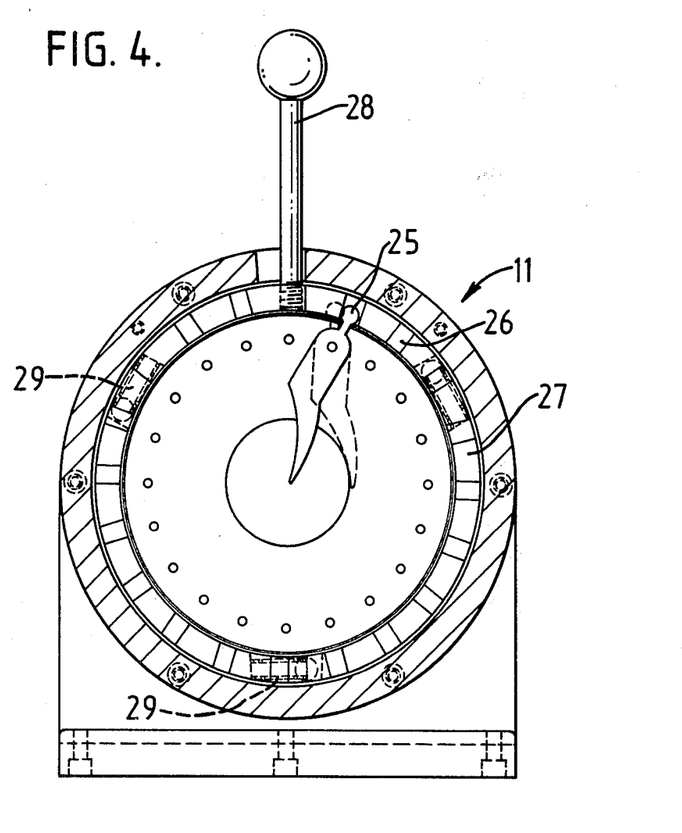
FIG. 4 is a front section of the end cleaning attachment.

Referring now particularly to FIGS. 3 and 4 the end cleaning attachment 11 comprises a cylindrical chamber 20 having a high pressure water manifold 21 at one end. The high pressure water manifold 21 is axially movable to accommodate different configurations of pipe and is provided with four radially disposed jets 22 (only one shown) directed inwardly towards the axis of the water manifold 21. The water manifold 21 is locked in axial position by locking screw 23.

At the other end of the chamber 20 is an adjustable pipe receiving opening defined by twenty pivotally mounted blades 24 (only one shown). The blades 24 are mounted upon the body of the end cleaning attachment 11 and each have a projecting head 25 which is received in a respective slot 26 of a movable ring 27. The ring 27 is manually operable by means of handle 28 and is biassed into a closed position by three springs 29. A bearing strip 30 ensures smooth movement between the limits of movement illustrated by the full and dotted lines of blade 24 in FIG. 4.

Figure 2:
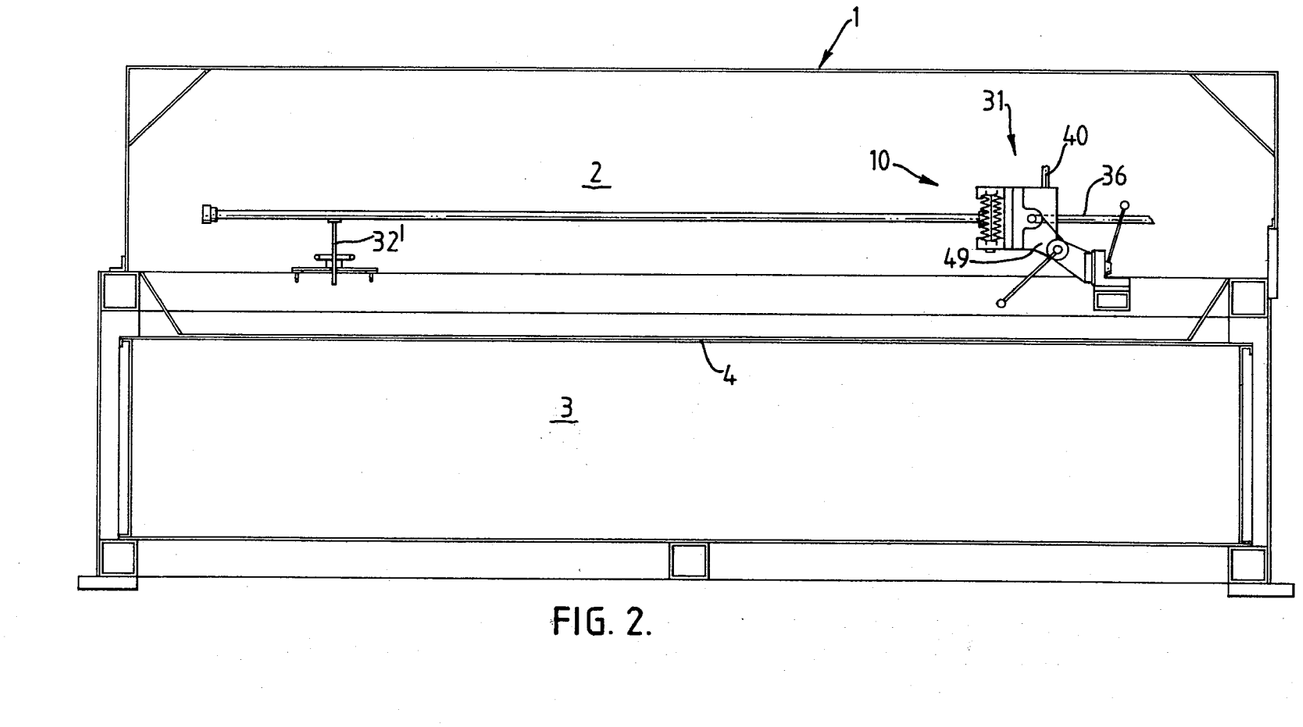
FIG. 2 is a front elevation of the treatment chamber partially broken away for clarity.

The pipe-receiving area 2 itself is suitably about 3 meters long enabling 2 meter pipes to be treated with ease. At one end of the pipe-receiving area 2 is a pipe-treatment manifold 31, the other end of the area 2 including an adjustable pipe support 32' for use when required. The pipe-treatment manifold 31 is movable 90° about a longitudinal axis for accommodating varying pipe shapes.

Figure 5:
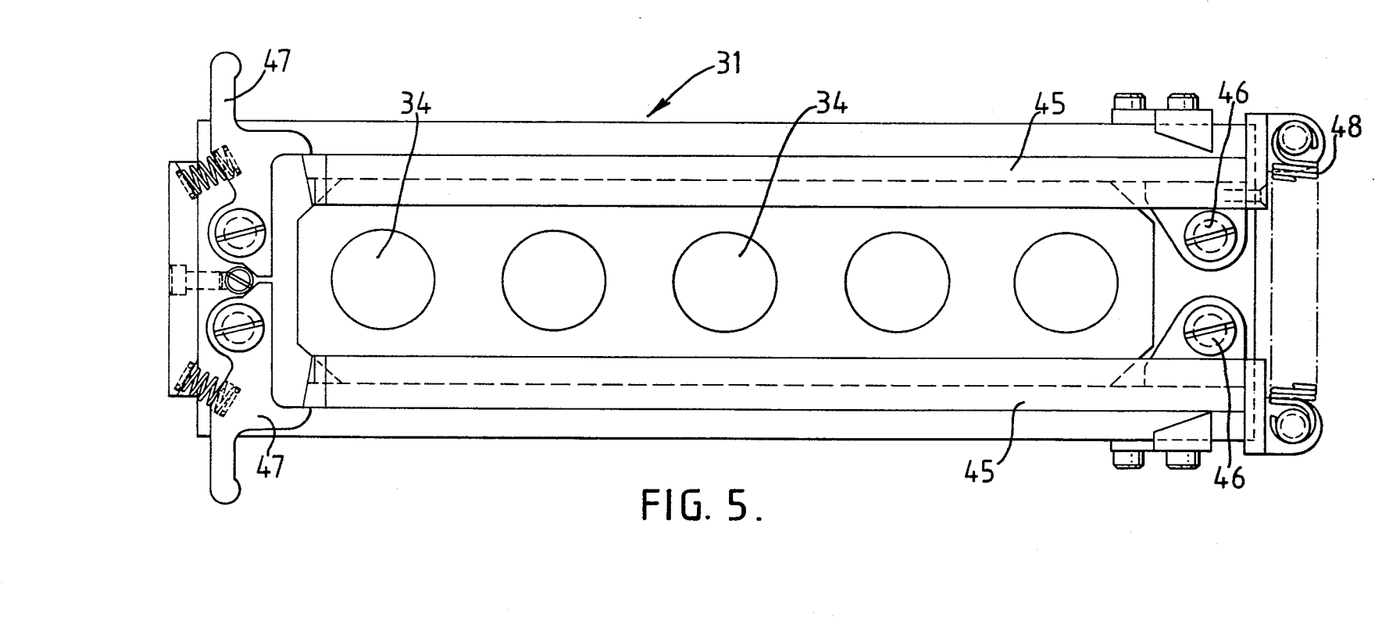
FIG. 5 is a front view of the treatment manifold.
Figure 6:
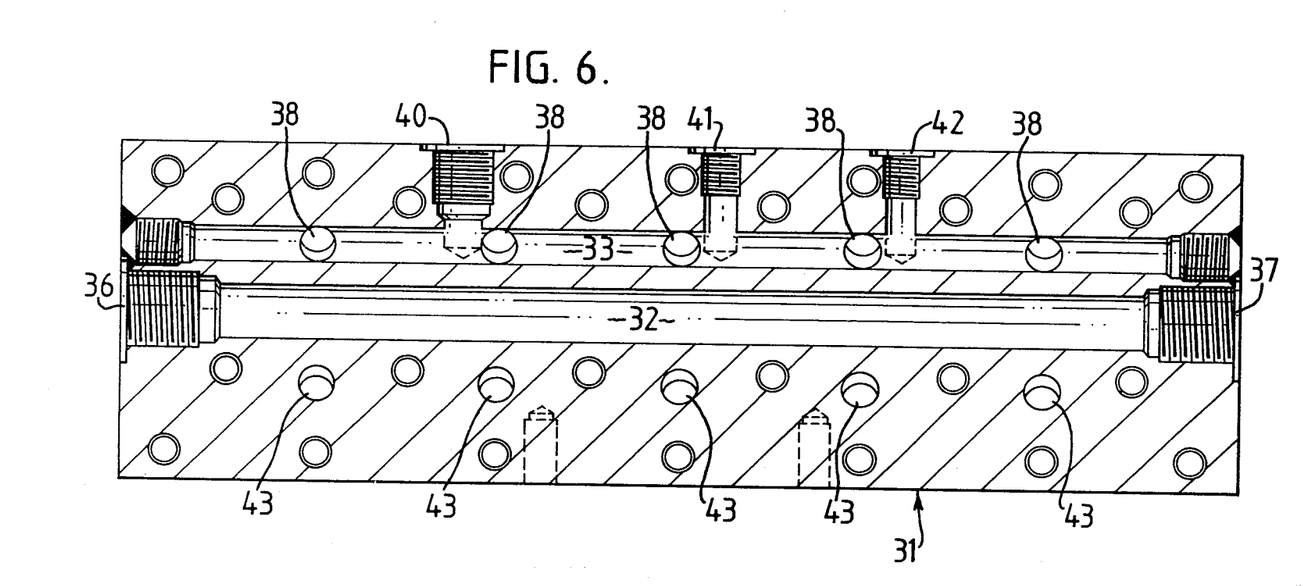
FIG. 6 is a longitudinal sectional side elevation of the treatment manifold on 6—6 in FIG. 7.
Figure 7:
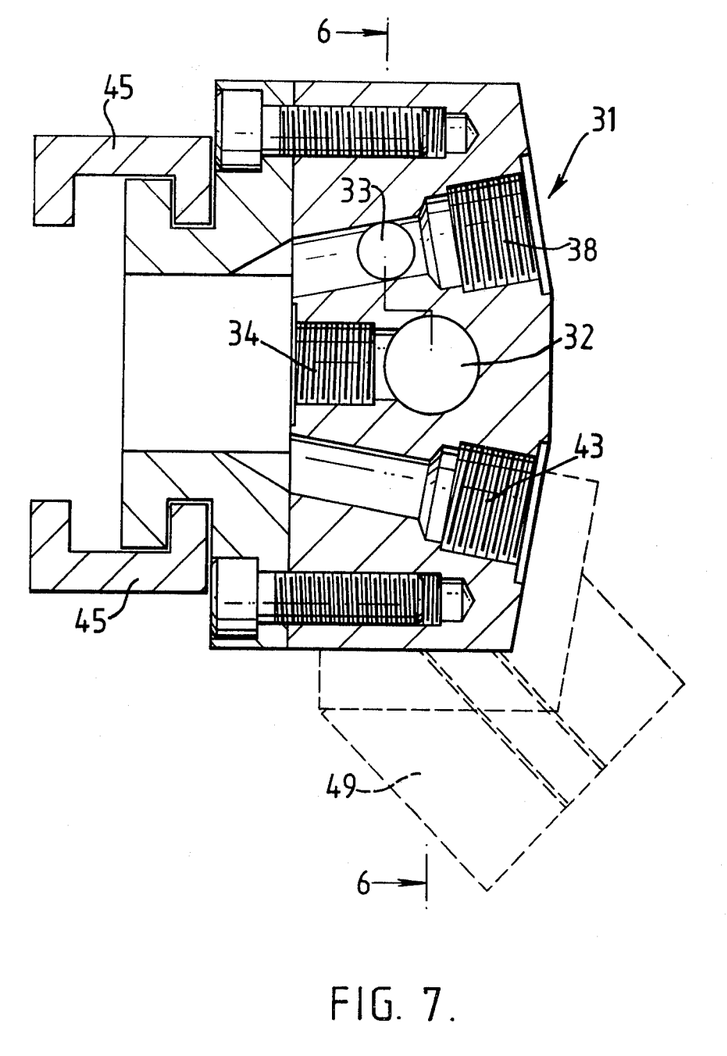
FIG. 7 is a transverse cross-section.

Referring now particularly to FIGS. 5, 6 and 7 the pipe-treatment manifold 31 includes a main longitudinal bore section 32 and a secondary bore 33 which is plugged at both ends. Drilled into the main bore 32 are five jetting apertures 34 which receive high pressure water cone jets 35 (see FIG. 8). The cone jets 35 are supplied with high-pressure water through a one-way valve-controlled, high-pressure water inlet 36 at one end of the bore 32, the other end 37 forms the inlet for compressed air for air-drying, the inlet 37 also normally closed by a non-return air valve (not shown).

Figure 8:
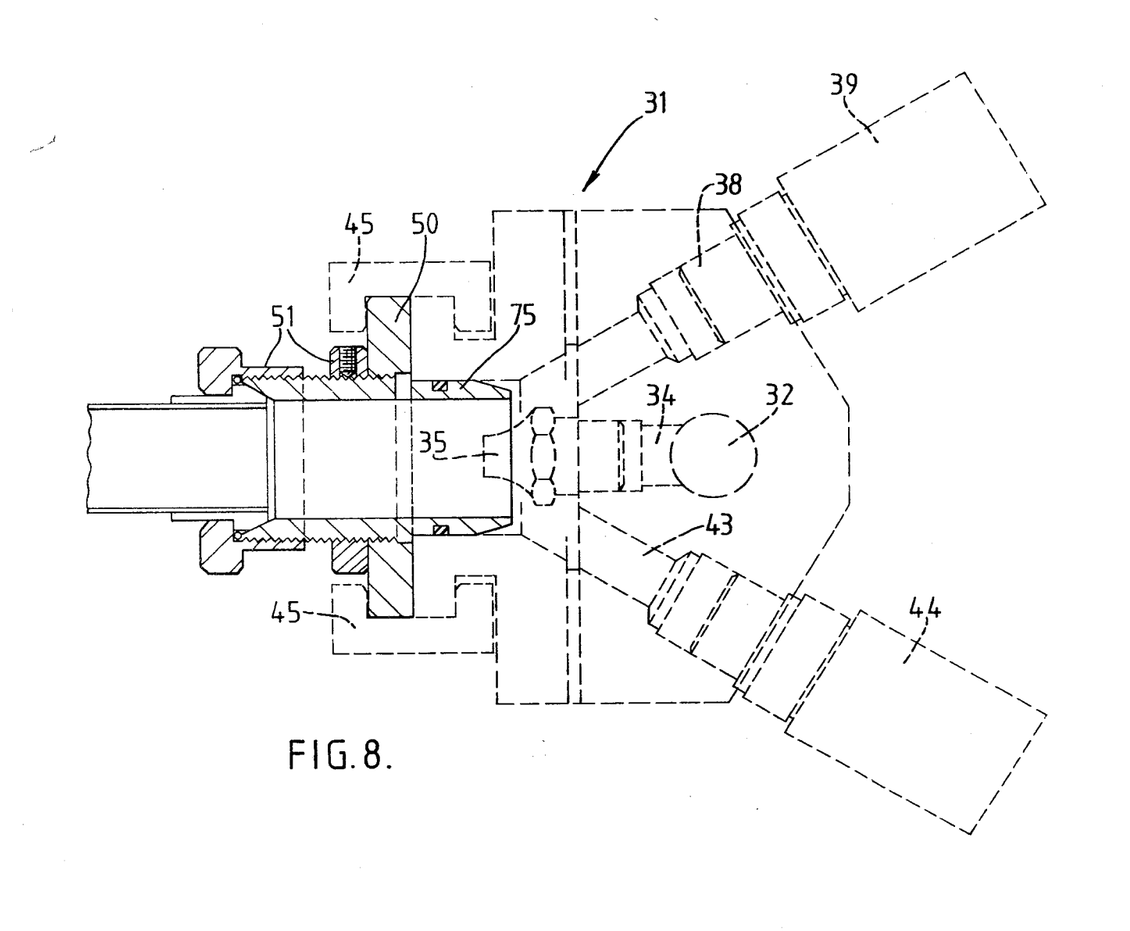
FIG. 8 is a partially diagrammatic transverse showing a pipe connected to the manifold.

The secondary bore 33 has five transverse apertures 38 drilled into it and out to the rear of the manifold 31. The rear opening of those apertures 38 is closed by a non-return valve 39 (FIG. 8). In addition three further bores 40, 41 and 42 are drilled from the top of the manifold 31 into the bore 33. These bores 40, 41 and 42 form respectively the lower pressure water filler inlet, the pressure test inlet and the pressure test relief. Finally, five further apertures 43 are drilled from front to back of the manifold 31 below the cone jets 35. These apertures 43 are each closed at their rear by a non-return valve 44 in a similar manner to the apertures 38.

On the front of the manifold 31 are upper and lower clamps strips 45 which are pivoted to manifold 31 at 46. The clamp strips 45 are normally held in the position shown in FIGS. 5 and 7 by spring biassed toggle levers 47. The two clamps strips 45 are united at their pivoted ends by two springs 48 which serve to limit movement of the clamp strips 45. FIG. 7 shows in dotted lines one of the brackets 49 which forms the pivotal mounting for the manifold 31.

In order to accommodate various sizes of pipe an adaptor plate 50 (FIG. 8) is provided which has five apertures corresponding to jetting apertures 34. The adaptor plate 50 is held in position by clamps 45 and the provision of a plurality of these plates 50 means that pipes of diameters ranging from 5 mm to 25 mm can be treated. The pipes to be treated are secured to the adaptor plate 50 by screw couplings 51.

Figure 9:
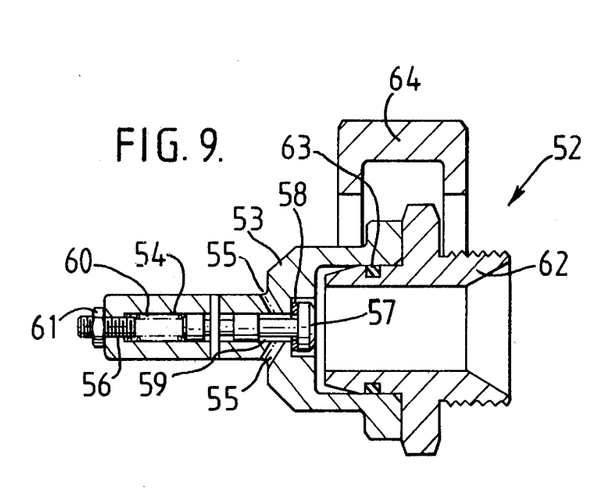
FIG. 9 is a sectional side elevation of a preferred form of automatic bleed valve.

During pressure testing of pipes received in the treatment chamber 1 the ends of the pipes remote from the manifold have to be closed. For this purpose special valves 52 are provided one of which is shown in FIG. 9. The valve 52 comprises a body 53 having an axial bore 54 to which transverse branch bores 55 are connected. The axial bore 54 receives a plunger 56 having ahead 57 with a sealing ring 58 which may seal against the mouth of bore 54. Adjacent the head 57 of the plunger 56 is a portion of reduced cross-section so that a path 59 to transverse branch bores 55 is provided when the valve is open. The plunger 56 is normally held in an open position by a coil spring 60 the strength of which can be adjusted by manipulation of end nut 61.

In order to connect the valve to the end of a pipe a tubular adaptor 62 is provided one end of which is slidably received within the body 53, O-ring seal 63 providing the necessary seal between the adaptor 62 and the body 53. The other end of the tubular adaptor 62 is screw-threaded for simple engagement with the nut provided on pipes being tested. In order to lock the tubular adaptor 62 and the valve body 53 together a removable clamp 64 is simply slid transversely over the two parts to engage respective projections on each part.

Figure 10:
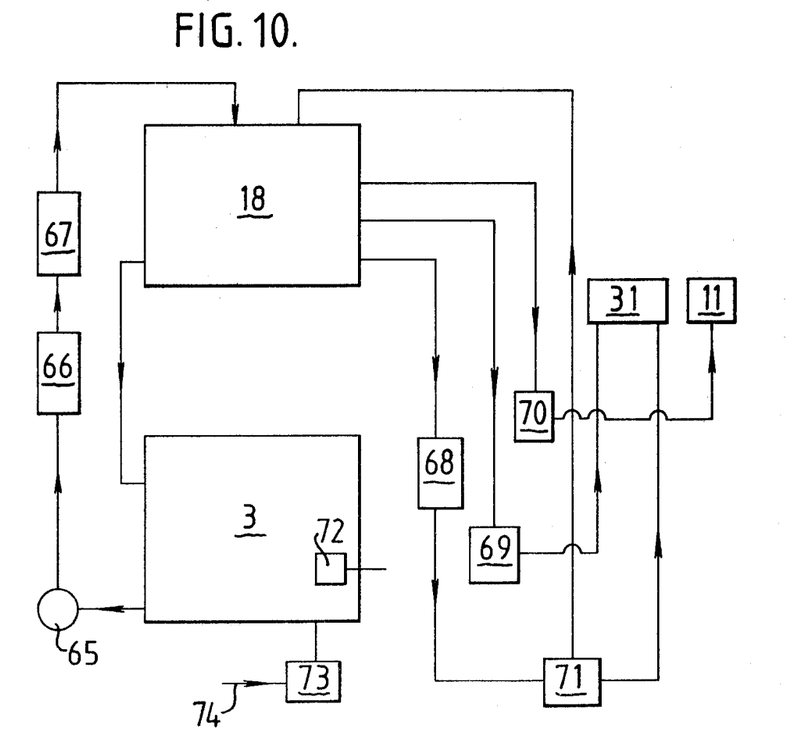
FIG. 10 is a block diagram of the fluid circuits.

Referring now to FIG. 10 water is kept continually circulating between the water tank 3 and the header tank 18 by means of circulation pump 65. This pump also causes the water to pass through first and second stage filtration 66 and 67. The first stage filtration 66 is a high rate sand filter filtering at a rate of 30 g.p.m. which receives effluent directly from the wash area and forces it through a deep bed of graded sand filtering the water down to a level of 16/20 microns. The second stage filtration 67 comprises a ceramic type filter, filtering at a rate of 16 g.p.m., which further refines water down to a level of approximately 5 microns.

In a second circuit water is continually drawn from the header tank 18 by means of high pressure water jetting pump 68, low pressure pump 69, and medium pressure pump 70. High pressure water jetting pump 68 feeds water at pressures up 8000 psi to a diverter valve 71 which, according to demand, either directs the water to the high pressure water inlet 36 of manifold 31 or back to header tank 18. Low pressure pump 69 is self-bleeding and supplies water to filler inlet 40 via a non-return valve as required. Medium pressure pump 70 is also self-bleeding and supplies water at about 500 psi to the end washing attachment 11. The water from the manifold 31 and end washing attachment 11 is returned to the washing tank 3 for re-use. In order to ensure that the amount of water in use is sufficient a level switch 72 is provided which is operable to open solenoid valve 73 in mains supply line 74 when the level drops below that level.

In use an operator will work with pipes in batches of similar size and shape. The first batch of pipes may be inserted one at a time on either end into the end cleaning attachment 11 to clean the retaining nut with low-pressure water (500 psi/2.5 g.p.m.). The operator will then mount five of the batch of pipes on a suitable adaptor plate 50, block the other end of the pipes with a self-bleeding valve 52, and, depending upon the length of the pipes being treated, position the pipe ends on support 32'.

Once the five pipes are mounted, the operator sets the attitude of the main treatment manifold 31 in the cabinet to suit the angles of the pipework. Having set and locked the manifold 31 the operator then inserts the spigots 75 (FIG. 8) mounted on the adapted plate 50 into the cooperation holes on the fixed manifold section 31 and clamps the adaptor plate 50 to the manifold 31 by means of clamp strips 45.

With the pipes suitably positioned the operator closes the counterbalanced canopy 5 and clamps it down. The apparatus is now ready and the pipes are filled with low pressure water by pump 69 and via inlet bore 40: the automatic bleed valves 52 bleeding air from the pipes until all the air has been evacuated and the water pressure is sufficient to overcome the pressure of springs 60 and thereby close the valves.

The first operation is pressure testing the pipes up to a desired pressure: this is done by pressurising the filled pipes by applying pressure via the inlet bore 41 with the relief bore 42 closed.

The desired pressure, e.g. up to 8000 psi, is then held for the required time whereupon the relief valve in bore 42 is opened to release the pressure within the pipes. The pressure applied to the pipes under treatment is shown on pressure gauge 14 on control panel 12. Also the pressure is transduced to a paper tape printing machine giving an electrical output which will vary in direct relation to the pressure and which can be signalled on the continuous reel of test certificates as a printed line which, in the case of a successful pressure test, will be set at the required pressure: this is all effected at 16 in a manner known per se. Therefore, the operator brings the system up to the required test pressure by reference to the pressure gauge which, when achieved, is held set. The paper tape read-out is then actuated and it is run for the required time (2 minutes). The operator watches the operation through the viewing panel 8 watching the water leakage or loss of pressure indicative of pipe failure. Whilst pressure testing is taking place the next five pipes can be mounted onto a further adaptor plate 50 on the work table 10.

At the conclusion of the pressure test the relief valve in bore 42 is released which in turn releases the interlocked catches on the canopy 5. The operator then can either remove the pipes which have been tested and replace them with the second batch and continue this operation until he has pressure tested the complete batch, or release the quick release part of the automatic bleed plugs and continue with the washing and drying cycle. The question whether he continues with the process to wash and dry or goes through the complete batch and pressure test them all normally will be determined in operation by the quantity of pipes which the operator has to process in any one batch.

However, once pressure testing has taken place and the plugs removed, the pipes are washed with high-pressure water supplied to the high-pressure water inlet 36 by appropriate actuation of the diverter valve 71. The water issues through the cone jets and the volume of water used is determined by the size of the largest pipe is 25 mm. In order to effectively clean this size over five pipes will require approximately 15 gallons per minute at 4500 psi. The dirty water from the pipes is collected in the water collector tank 3 and then passed for filtration as described above. Once washing is complete the supply of high-pressure water is terminated, and compressed air for air-drying is introduced through inlet 37. As the drying air is compressed air it is jetted through cone jets 35 and this air draws further air through non-return valves 39 and 44 to increase the drying effect: dying being both by evaporation and by physically forcing the water off the surface. The bores 40 and 41 are provided with non-return valves as explained above in order to prevent the pressure of jetting of compressed air drawing water through these bores. The air is suitably at a pressure of about 100 psi.

The apparatus of the present invention makes it possible at the same station:

(a) to pressure test a variety of pipework in varying shapes and lengths. the maximum overall length of pipe being approximately 6 ft. and the internal diameter of the pipes varying from 5 mm to 25 mm. The pressure testing being infinitely variable between 500 to 8000 psi;

(b) to clean the pipes to a high cleanliness specification;

(c) to dry the same pipes.

The machine is self-contained, recirculating the cleaning and testing water filtering it down to the required level. It also provides a printed read-out of the pressures achieved and held during the pressure testing, calibrated against a time base. This printed read-out is in the form of a test certificate on a continuous reel and can be turned off and duplicated for each of the five pipes in the batch. The automatic bleed valves 52 also considerably aid operation since no manual operation of end valves is required in order to accomplish pressure testing.

I claim:

1. A method of pressure testing and cleaning a pipe, having first and second ends, at a single station comprising the steps of:
   (a) providing a treatment manifold having at least one pipe receiving location;
   (b) positioning the first end of the pipe on the treatment manifold at said at least one pipe receiving location;
   (c) providing closure means at the second end of the pipe to seal off said second end of the pipe;
   (d) supplying fluid to the pipe through the treatment manifold;
   (e) pressuring the pipe to a required desired value;
   (f) sensing the pressure level within the pipe so as to register a pressure drop indicative of pipe failure;
   (g) releasing pressure within the pipe;
   (h) removing said closure means from the said second end of the pipe; and
   (i) washing the pipe with water at high pressure above 500 psi supplied through the treatment manifold.

2. A method of pressure testing and cleaning a pipe according to claim 1 wherein the pressurizing fluid is water and the closure means is a self-bleeding valve so as to automatically bleed air within the pipe on supply of water to the pipe.

3. A method of pressure testing and cleaning a pipe according to claim 2 wherein the water used is recycled for reuse.

4. A method of pressure testing and cleaning a pipe according to claim 1 or 2 including the further step of (j) introducing air into the pipe to air-dry the pipe with air supplied through the manifold.

5. A method of pressure testing and cleaning a pipe according to claim 4 wherein compressed air is supplied to the manifold for drying the pipe and said compressed air simultaneously draws in additional air to enhance the drying effect.

6. A method of pressure testing and cleaning a pipe according to claim 1 wherein the pressure testing and washing steps are effected without removal of the pipe from the manifold.

7. A method of pressure testing and cleaning a pipe according to claim 1 comprising the initial step of (k) cleaning the said first and second ends of the pipe with pressurized water prior to the positioning of the pipe on the treatment manifold at said pipe receiving location.

8. Apparatus for pressure testing and cleaning a pipe having first and second ends comprising a treatment manifold, means for locating the first end of the pipe on the treatment manifold at a pipe receiving location, means for supplying fluid to the pipe via said treatment manifold, removable closure means for closing the second end of said pipe, means for pressurizing said fluid within the pipe, sensing means for sensing the pressure level within the pipe so as to register a pressure drop indicative of pipe failure, and means for washing the pipe with water at high pressure above 500 psi once the pressure test has been successfully completed and the closure means removed.

9. Apparatus according to claim 8 wherein the removable closure means includes a self-bleeding valve so as to automatically bleed air within the pipe during pressure testing with water.

10. Apparatus according to claim 9 wherein the self-bleeding valve is biassed into an open position until the pressure within the pipe is sufficient to overcome said bias and close the valve.

11. Apparatus according to claim 8 wherein the treatment manifold comprising a main bore, a valved inlet to the main bore for high pressure water, a first plurality of apertures opening into the main bore each for receiving a pipe to be treated, a secondary bore, a second plurality of apertures opening into the main bore and one into each of the first plurality of apertures, the means for supplying fluid to the pipe and the means for pressurising said fluid comprising first and second inlets into the secondary bore.

12. Apparatus according to claim 11 wherein the second plurality of apertures are also open to atmosphere via a non-return valve.

13. Apparatus according to claim 11 or 12 comprising a valved air inlet to the main bore for drying air.

14. Apparatus according to any one of claims 10 to 13 comprising an end cleaning chamber in which the ends of each pipe are cleaned prior to pressuration and washing, said end cleaning chamber including a pressure water manifold and a variable opening through which the ends of pipes are inserted for cleaning.

* * * * *